United States Patent [19]

Hardy

[11] Patent Number: 4,768,524
[45] Date of Patent: Sep. 6, 1988

[54] DEVICE FOR IMMOBILIZING A BONE STRUCTURE, ESPECIALLY INTENDED FOR ORTHOPEDIC USE

[76] Inventor: Jean-Marie Hardy, Chateau de Noailles, 19600 Larches, France

[21] Appl. No.: 17,884

[22] Filed: Feb. 20, 1987

[30] Foreign Application Priority Data

Feb. 28, 1986 [FR] France ................................ 86 02818

[51] Int. Cl.[4] .............................................. A61F 5/04
[52] U.S. Cl. ................................................. 128/92 Z
[58] Field of Search ........... 128/92 Z, 92 ZW, 92 ZZ

[56] References Cited

U.S. PATENT DOCUMENTS 4,365,624  12/1982  Janquet ............................. 128/92 Z Primary Examiner—John D. Yasko
Attorney, Agent, or Firm—Burgess, Ryan & Wayne

[57] ABSTRACT

Device for immobilizing a bone element, especially for orthopedic use, comprising pins or needles, passing through the element, mounted in supports themselves borne by two metallic rigid hoops surrounding the bone element and separated from one another by spacing braces having an adjustable length, each hoop having in straight cross-section an external outline presenting two flattened parallel portions 14, 15 respectively connected by two convex portions 16, 17 the supports of the pins or needles 3 borne by the hoop being constituted by laterally open parts having two wings comprising plane surfaces adapted to cooperate through plane sliding with the flattened portions of the hoop, these wings being joined by a concave portion matching the outline of one of the convex portions of the external outline of the hoop.

11 Claims, 4 Drawing Sheets

DEVICE FOR IMMOBILIZING A BONE STRUCTURE, ESPECIALLY INTENDED FOR ORTHOPEDIC USE

BACKGROUND OF THE INVENTION

1. Field of the Invention

The present invention concerns an external fixation and immobilization device for a bone element or structure in particular a human member, especially adapted for use in the method known as the ILIZAROV method.

2. Summary of the Prior Art

It is known that this method, which is classical and widely used in orthopedic surgery fields, consists in associating, to a bone element or structure or to two parts of such structure, intersecting needles or pins, passing in pairs through the bone element or structure and supported in precisely defined positions by a kind of external open-worked housing, comprising two rigid metallic hoops or hoop portions, surrounding the bone element and separated from one another by brace elements having an adjustable length maintaining them in steady fixed position at a suitable distance, the needles or pins passing through the bone structure being dependent upon these hoops or half-ring portions and immobilized thereupon in order to cooperate with the bone element in two distinct, separated and perfectly localized zones. Advantageously, the pins or needles are engaged in the supports bone by the hoops and disposed so that they are oriented according to the radii of the hoops, these supports furthermore comprising means adapted to exert a tension or a compression upon these pins or needles in order to apply to the bone element a suitable strain.

According to certain embodiments already known in the prior art of such attachment devices utilized for carrying out the ILIZAROV method, especially for the kind of such as those described in U.S. patent application Ser. No. 830,654 dated Feb. 18, 1986 in the name of the present application for an external fixation device adapted for orthopedic use, it has already been foreseen, in particular to constitute hoops by means of a tube having a circular cross-section upon which are engaged articulated collars, provided with immobilization means to lock them in any given position on these hoops, certain of these collars furthermore comprising means adapted to receive and immobilize the ends of the pins or needles of which the opposite ends cooperate with the elements for submitting these pins to tension.

This solution, which offers various advantages, especially as to the simplicity of production and the fact that it comprises a reduced number of pieces necessary for its application, thus allowing to achieve a relatively precise positioning of the needles or pins with respect to the bone element to pass through, nevertheless presents drawbacks. In particular, in this solution, once the hoops are immobilized in position after adjustment of the length of their spacing braces, it is no longer possible to modify neither the orientation in azimuth of the crossing pins or needles, which remain radially oriented relative to the hoops nor their positioning in height, the fixation collars being directly intersected these pins or needles of which they are fastened.

Furthermore, due to the rounded cross-section of the hoops, the tightening of a collar on the hoops in order to immobilize it, does not always allow, under the effect of rotation torque created when a tension or compression strain is exerted on the pin or needle borne by the collar, to prevent the collar from turing on the hoop and shifting even slightly, the orientation of the corresponding pin or needle. Thus, this does not work properly and consequently this can be particularly prejudicial during reduction of a fracture or during treatment of a fracture by osteosynthesis.

The present invention concerns improvements proposed by a device for immobilizing a bone structure of element of this kind recalled herein-above, in particular of the type described in the above-mentioned U.S. patent application which, by overcoming the drawbacks of the solution described, offers complementary advantages to those already resulting from the structure thus envisaged.

According to the invention, the device concerned is characterized in that each hoop presents in cross section an external outline presenting two parallel flattened portions, connected respectively by two convex portions, the supports of the pins or needles borne by the hoops being constituted by lateral open blocks and presenting two wings comprising plane surfaces adapted to cooperate by plate sliding on the flattened portions of the hoop, these wings being associated by a concave portion matching the outline of one of the convex portions of the external outline of the hoop.

Due to these dispositions, the support blocks of the pins or needles interlock easily by the lateral side of the hoop intended to support them and, once placed in position, are no longer subjected to relative rotation around the corresponding hoop during the strains of these pins or needles, the plane bearing of the wings of the blocks on the flattened portions of the hoop preventing any shifting with respect to one another in the plane containing the pin or needle supported by the block.

According to one particular characteristic, each block mounted on a hoop comprises in one of its wings cooperating with one of the flattened portions of the hoop, a transversal bore, extending parallely to the flattened portion, internally threaded and within which is adapted to be driven a screw the end of which protrudes within a hole perpendicular to the bore, provided at the end of the wing of the runner and inside which is mounted a stop ball protruding from the end of this hole in order to issue through an opening having a smaller diameter delimited by a narrowing of the hole, so that the displacement of the screw ensures the blocking of the ball against the hoop and the immobilization of the runner.

According to another characteristic of the invention, at least one wing of each runner externally presents a tenon or a mortise, adapted to be respectively engaged in a mortise or tenon having the same outline, provided in a support comprising a passage crossed through by an externally threaded sleeve or sheath, itself axially provided with a narrow channel for the penetration of a pin or a needle locked with respect to the sheath, the support furthermore comprising a transversal housing in which is confined a nut cooperating with the external threaded part of the sheath whereas the passage of said sheath internally comprises a wedge or cleat sliding in axial groove provided in the external surface of the sheath, so that the rotation of the nut provokes the displacement of the sheath in the support and the putting under tension or compression with respect to the bone element of the corresponding pin or needle. According to a complementary characteristic, the pin or needle is locked in the narrow channel of the sheath by means of a screw engaged in a radial bore of a head corresponding to the end of the sheath.

According to another advantageous characteristic of the invention and in function especially of the particularly useful requirements of height adjustment of each support on one of the hoops of the device, each runner is associated to a wedge borne by one of the wings of the block, the correction between the wedge and the runner being achieved by means of an axis borne by the wedge and engaged in a bore provided in the wing of the runner, this bore extending perpendicularly to the flattened portions of the hoop. Preferably, the locking of the wedge with respect to the runner is carried out by a radial blocking screw, crossing a threaded hole provided in the body of the block and issuing into the passing bore of the shaft borne by the wedge. Usefully, the axis presents an intermediary groove into which penetrates the end of the blocking screw.

According to a further characteristic of the device of the invention, each hoop is advantageously constituted by means of the two half-hoops, adapted to be jointly associated by a set of two rectilinear extension pieces, of variable length in each set, presenting in straight cross-section an outline identical to that of the hoop, each extension piece comprising at its ends connecting members cooperating with the opposite ends of each half-hoop. Preferably, each connecting member is constituted by a protruding tip, borne of the half-hoop or the extension piece and penetrating within a housing of the same outline respectively provided in the extension piece of the half-hoop, the blocking of the extension piece and of the half-hoop after engagement of the tip in its housing being performed by at least one transverse screw.

According to yet another embodiment, each of the hoops is also associated to an assembly of double collars, each constituted by two pairs of jaws, connected by a common transverse axis, one of these pairs of jaws being adapted to tighten the hoop and the other end of an adjustable spacing brace, mounted between the two parallel hoops and extending perpendicularly at the plane of these hoops. Advantageously, each spacing brace is constituted by two parts disposed in the extension of one another and associated to an intermediary stretching device or turnbuckle, comprising a rod of which the two opposite ends are threaded in opposite directions and cooperate respectively with two nuts integral with the ends opposite the two parts of the spacing brace.

According to another particular characteristic, one of the two pairs of jaws of the double collar can be fastened to a bar comprising successive passages for the fixation of a pin or needle support, cantilevered with respect to the hoop.

BRIEF DESCRIPTION OF THE DRAWINGS

Other objects, features and advantages of an immobilization device according to the invention will become apparent from the following description of the several embodiments, given by way of non-limitative illustration, with reference to the appended drawings in which.

DETAILED DESCRIPTION OF THE DRAWINGS

Figure 1:
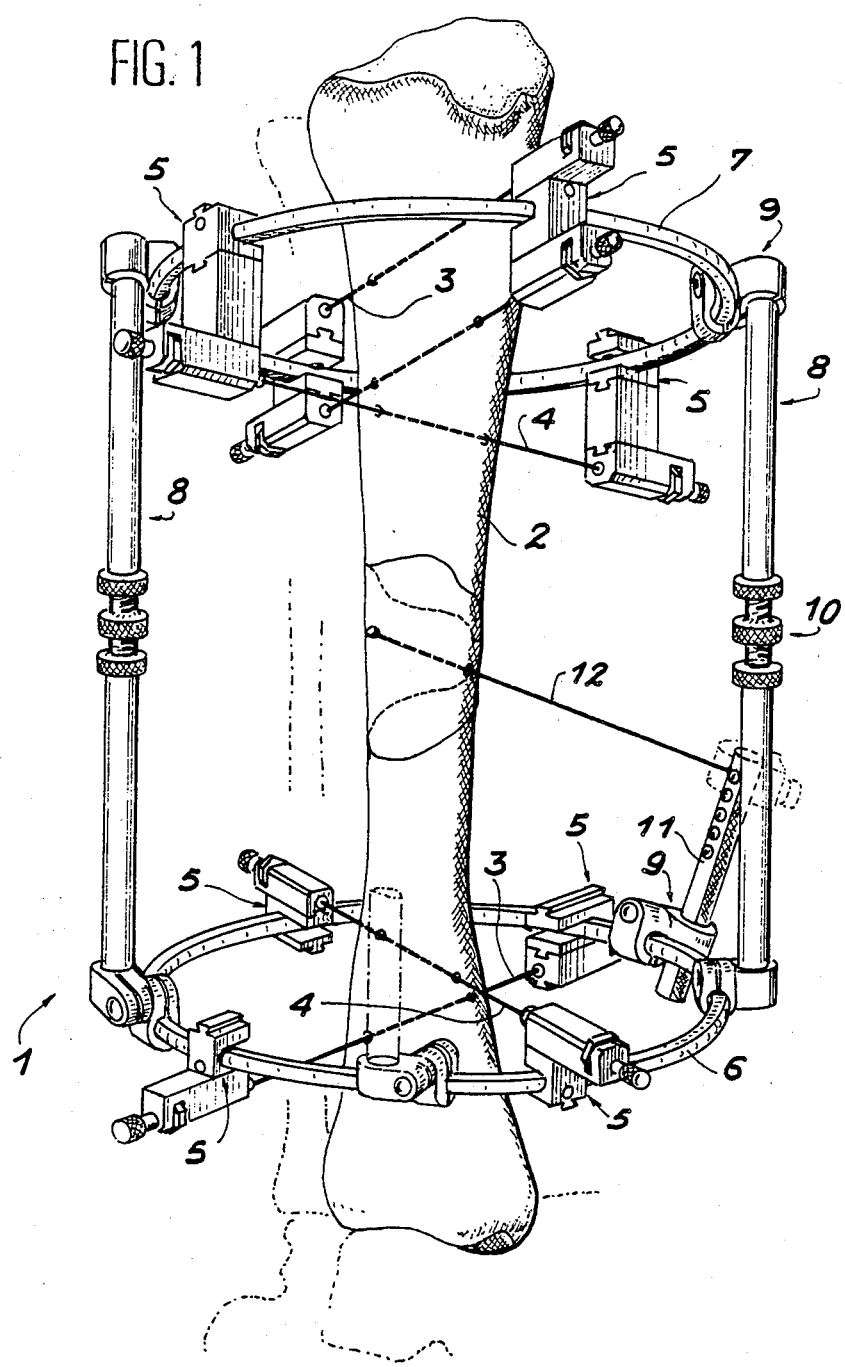
FIG. 1 is a perspective view of a fixation device according to the invention, representing locking a long bone elements, mounted therein.

On a perspective view illustrated on FIG. 1, the fixation device according to the invention is designated as a whole under reference 1 and is more particularly intended for the immobilization of a bone element 2, represented in a vertical position inside the device.

In order to lock element 2, the device comprises according to a known disposition carried out in a classical manner in the treatment method known as the ILIZAROV method, two sets of two needles or pins, respectively passing through the ends of the bone element 2 and designated on the drawing in each set under the reference numerals 3 and 4. Each needle 3 or 4 is immobilized inside a support 5 the embodiment details of which will be described herein-below, the supports being mounted respectively on two hoops 6 and 7 extending according to two planes substantially parallel and disposed adjacent to the ends of the bone element 2 in order to allow the device according to the invention to ensure the appropriate immobilization of this latter.

Hoops 6 or 7 are maintained at a suitable spacing distance through the intermediary of adjustable spacing braces 8, the ends of which being respectively connected by double collars 9 to the hoops 6 and 7. Especially, each spacing brace is preferably formed of two parts disposed in the extension of each other and comprises an element 10, forming a stretching device or turnbuckle allowing to adjust the spacing of these two parts and the length of the corresponding spacing braces in order to allow to vary as required the distance separating the two hoops 6 and 7. Other collars 9 are also mounted on hoops 6 and 7 in order to ensure the immobilization of the support bars such as 11, cantilevered with respect to these collars and allowing the fastening of other pins or needles 12, passing in this case slant-wise through the bone element 2, these complementary needles 12 generally being disposed between the planes of the parallel hoops 6 and 7.

Figure 2:
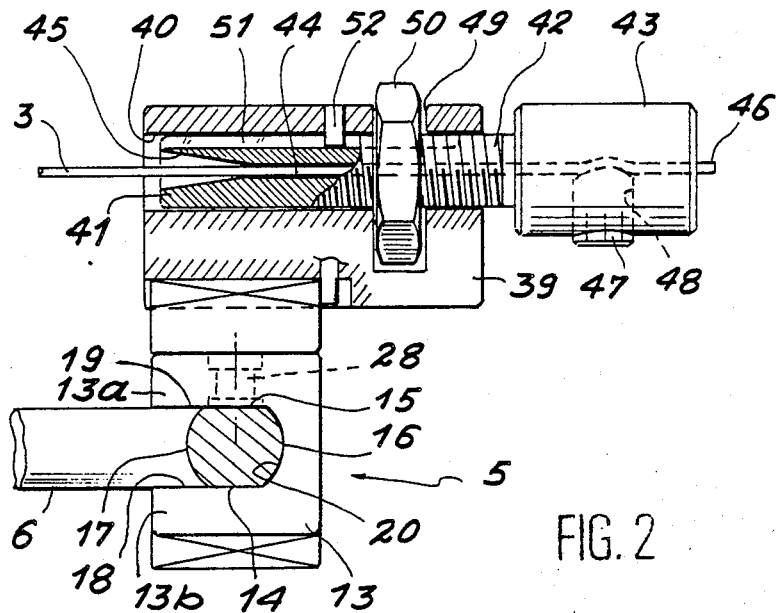
FIG. 2 is a view in transversal cross-section on a larger scale of the support of a needle or a pin passing through the bone element borne by the device.

FIG. 2 illustrates on a larger scale the partial detail of the embodiment of a support element 5, mounted for example on one of the hoops 6 of the device. Each support 5 thus comprises a block 13, adapted to be interlocked by its two wings 13a and 13b on two flattened portions 14 and 15 provided on the hoop 6, these flattened portions 14 and 15 being connected to each other by convex portions 16 and 17 substantially demi-cylindrical. With this aim, the block 13 presents an open housing delimited by two wings 13a and 13b, the plane surfaces 18 and 19 of which are adapted to cooperate through plane sliding with the flattened surfaces 14 and 15, the surfaces 18 and 19 being themselves connected by a concave portion 20 of which the outline is adapted to substantially match that of the convex portion 16 connecting, in the hoop 6, the flattened portions 14 and 15.

Figure 3:
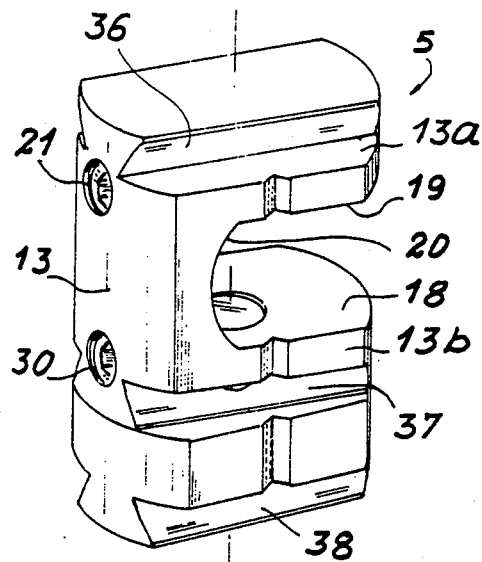
FIG. 3 is a perspective view of a runner according to the embodiment of the pin or needle support, according to FIG. 2.
Figure 4:
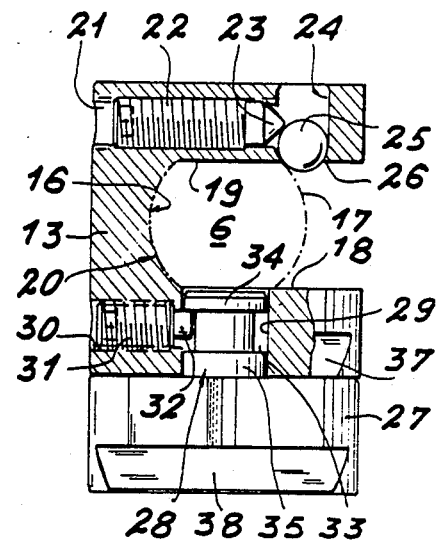
FIG. 4 is a transversal cross-section view of a block illustrated on FIG. 3.

As will be seen more particularly on FIGS. 3 and 4, each block 13 advantageously comprises in one of its wings a transverse bore 21 in which is mounted a screw 22, adapted to cooperate with a suitable machined threaded part inside the bore, this screw 22 presenting one end 23 issuing inside a hole 24 extending perpendicularly to bore 21. Inside this hole 24 is confined a ball 25 which slightly projects beyond an opening 26 delimited by a corresponding narrowing of the hole 24 and provided at the lower end of this hole in the direction of the wing 13a of the block 13 under which is engaged the corresponding flattened part of the hoop 6, this ball 25 urged towards the bottom by the end 23 of the screw 22 allowing, once the runner is suitably engaged on the hoop and especially with its plane surfaces 18 and 19 resting slidably on the flattened portions 14 and 15, to block this part such as illustrated more particularly on FIG. 4.

According to the invention, each of the blocks 13 or only certain of them can be advantageously associated to a thickness wedge 27, adapted to be fixed on one of the wings of the corresponding block by means of a stud or a transverse axis 28 engaging in a passage 29 provided in one of the wings of the block. There furthermore comprises a second transversal bore 30, parallel to the bore 21 and in which is mounted a screw 31 presenting at the end a lug 32 for locking the axis 28 with respect to the block, by engaging in an intermediary groove 33 provided between two parallel edges 34 and 35 machined on the axis 28. Each of the blocks 13 comprises in one and/or other of its wings 13a and 13b notches adapted to allow the fixation of a block 39 for immobilizing the penetrating pins or needles 3 or 4, intended to immobilize the bone element 2. Furthermore, each wedge 27 also comprises, in its face opposite that applied against the block 13, an identical notch 38, for the case where the block 30 is to be mounted on the runner after placing in position that wedge, in order to adjust suitably its height.

With further reference to FIG. 2, it will be seen that the block 13, provided where necessary with wedge 27, can thus be associated to such a block support 39, which comprises a bore 40 inside of which is mounted a sheath 41. This presents, on its external surface, a threaded part 42 and is completed by a blocking head 43. This sheath also comprises an axial channel 44 presenting, at its end opposite the head 43, a flared opening 45, allowing the engagement of one of the penetrating needles, for example needle 3, this latter which is extended in the direction of the head 43 being rendered locked inside thereof at its end 46 by means of a blocking screw 47 engaged in a transverse threaded screw 48 provided in the head 43.

The support block 39 furthermore comprises a median housing 49, inside of which is mounted a confining nut 50 cooperating with the threaded part 42 of the sheath 41. This sheath 41 further comprises a longitudinal groove 51 in which is adapted to slide a cleat 52, so that the rotation movement of the nut 50 on the threaded part 42 provokes the axial displacement of the sheath 41 inside the bore 40, thus allowing to exert, on the pin or needle 3 passing through the bone element 2, an appropriate tension or compression effort.

Figure 5:
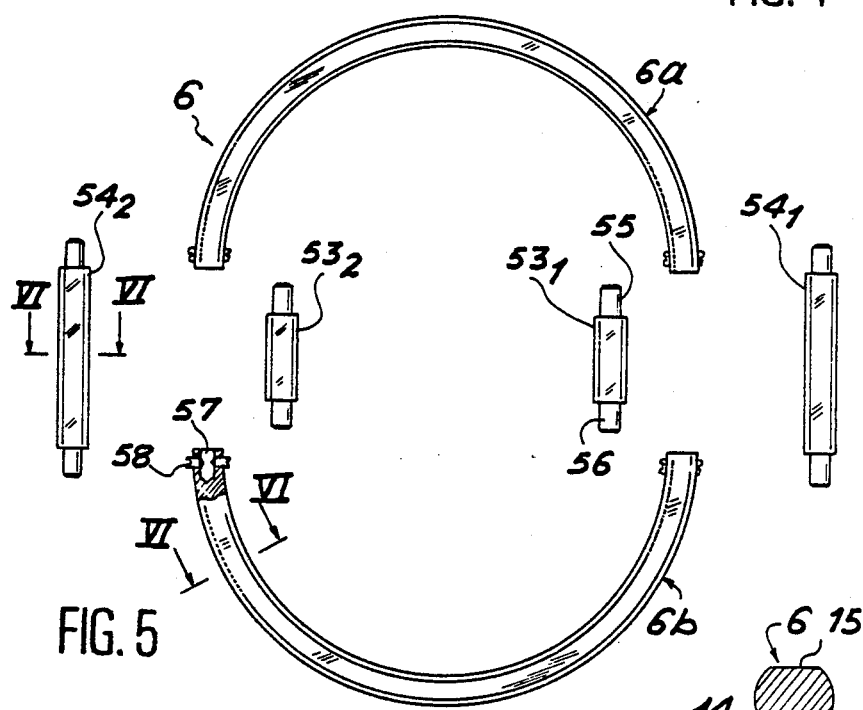
FIG. 5 is a view from above on a smaller scale of a fixation hoop of the device according to FIG. 1, represented constituted by two half-rings joined by extension pieces according to various embodiments.
Figure 6:
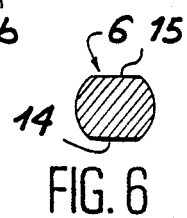
FIG. 6 is a cross-section view of one of the extension pieces illustrated on FIG. 5.

FIGS. 5 and 6 illustrate another embodiment detail of the immobilization device according to the invention, concerning the particular structure of each of the hoops 6 or 7 allowing to ensure the fixation of the supports 5 of the penetrating needles 3 and 4.

In the view represented on these figures, the lower hoop 6 for example is constituted by two half-rings 6a and 6b, connected to each other by a set extension pieces, such as $53_1$ and $53_2$ or $54_1$ and $54_2$, each pair of extension pieces presenting the same longitudinal dimension. These extension pieces each comprise end tips, respectively 55 and 56 adapted to be engaged in seats such as 57 provided inside the half-rings 6a and 6b in their opposite ends, these extension pieces being furthermore adapted to be locked, once they are mounted on the half-rings, by means of lateral blocking screws 58, cooperating with preceding seats 57.

Figure 7:
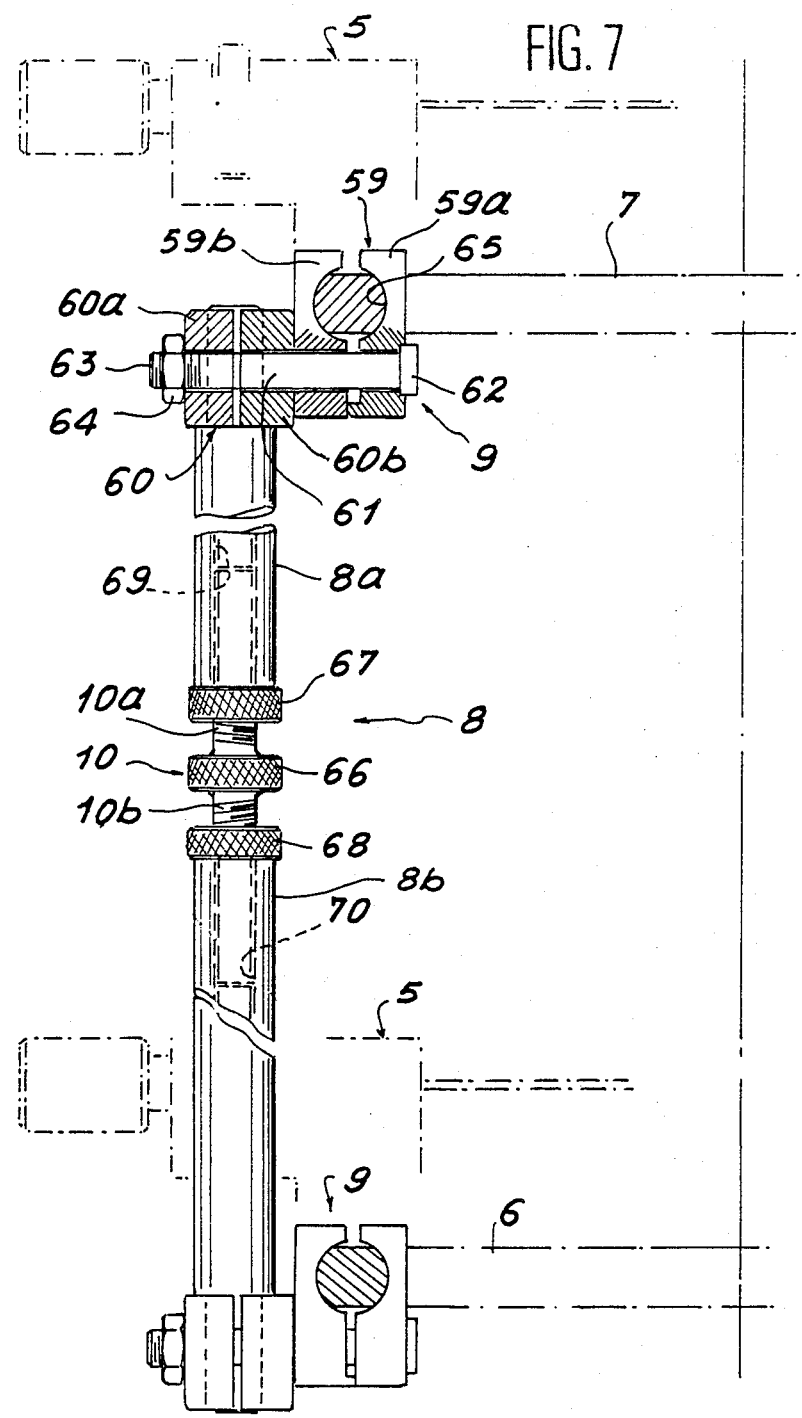
FIG. 7 is a view in elevation and in partial cross-section of a spacing brace used in the device according to FIG. 1 in order to maintain a determined distance between the fixation hoops.

FIG. 7 illustrates furthermore more particularly the embodiment detail of double collars 9, ensuring the mounting on the hoops 6 and 7 of the spacing braces 8 and the elements 10 which allow to ensure the adjustment in length of these spacing braces and consequently the appropriate displacement of these hoops with respect to the length of the element 2.

More particularly, each double collar 9 is in this example constituted by two adjacent elements, respectively 59 and 60, formed by two pairs of jaws 59a and 59b on the one hand, 60a and 60b on the other hand, these elements interacting by means of a common axis 61, comprising a stop head 62 and a threaded end 63, opposite the head 62 and on which is engaged a blocking nut 64. Each pair of jaws, for example pair 59a and 59b, delimits a housing having a substantially circular form 65, adapted to be engaged, for example, on the convex portions 16 and 17 of one of the hoops 6 or 7, the other pair of jaws 60a and 60b thus directly cooperating with the corresponding end of the spacing brace 3. Furthermore, and in order to allow adjustment of length of the mounting and to adjust the distance that separates the hoops 6 and 7, this spacing brace is formed of two parts 8a and 8b; disposed in the extension of one another and at the end of which are welded two nuts 67 and 68 cooperating with the threaded ends 10a and 10b of the corresponding adjusting element 10. This element comprises in particular a milled knob 66, allowing to rotate the element 10 inside the two housings 69 and 70 provided in the parts 8a and 8b of the spacing brace, the ends 10a and 10b presenting threaded parts in counter directions which, when rotating in the nuts 67 and 68, produce as desired the moving apart or the drawing together of the two parts 8a and 8b, and consequently adjust the relative positions of the hoops 6 and 7.

Figure 8:
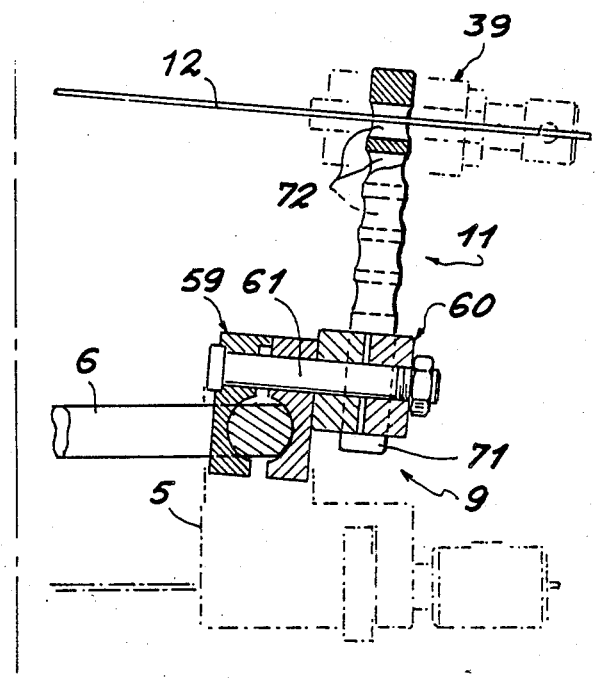
FIG. 8 is a detailed view of a double collar according to an embodiment of the device allowing the mounting of a bar for the cantilevered support of the fixation needles or pins.

FIG. 8 furthermore illustrates another detail of the embodiment of the locking device according to the invention in which certain of the double collars 9 mounted on one of the hoops 6 or 7 comprise, as previously, two fixation elements 59 and 60, provided in such a manner that the first fixation element is immobilized on the corresponding hoop while the second ensures the blocking in position of a cantilevered bar 11 and one end 71 of which is blocked in the pair of jaws of the element 60, this bar itself comprising a series of transverse holes 72 for the adjustable mounting in position of supports 39 of the same kind as those described herein-above. These supports 39 again immobilize a pin or needle 12, adapted to pass through the bone element 2 in a substantially median part of this latter, such as illustrated in FIG. 1, with in particular an orientation inclined on the vertical or more generally on the longitudinal direction of element 2, in order to exert on this latter a complementary tension or compression effort necessary for the treatment envisaged.

An immobilization device is thus produced which, while retaining the advantages of the device already described and claimed in U.S. patent application Ser. No. 830,654, in particular with reference to the simplicity of performance and the facilities of positioning and removing, contributes substantial improvements by increasing the efficiency of the conditions of fixation and blocking of the needles or pins on the hoops, as well as the faculties of the device for adapting to supports of these needles the position and orientation adjustment elements. The blocks, once mounted on the hoops, can no longer be rotated in their plane whatever the effort exerted on the corresponding needle, due to the outline with flattened portions provided for these pieces. Furthermore, the specified mounting for the thickness wedges on the blocks around a connecting axis allows to authorize, for the supports of the pins or the needles, a relative rotation in a plane substantially parallel to that of the hoop bearing the corresponding supports, in particular in order to allow an improved permutation of these needles in the bone element immobilized in the device.

It is well understood that the foregoing description while describing the various forms of pieces thus used is in no way limitative and on the contrary the present invention encompasses all variants and alternatives without departing from the scope and spirit of said invention.

What is claimed is:

1. A device for immobilizing a bone element, comprising:
    a first solid metal hoop surrounding the bone element;
    a second metallic hoop surrounding the bone element;
    a plurality of adjustable braces for connecting said first and second hoops in spaced, parallel relation by an adjustable distance;
    each hoop having an external cross-sectional configuration with two parallel flattened surfaces and two convex surfaces connecting the flattened surfaces;
    pin supports mounted on the hoops for supporting pins passing through the bone element, said pin supports including lateral open blocks mounted on a hoop;
    each block including:
        two wings with planar surfaces adapted to cooperate by planar sliding with the flattened surfaces of each hoop, said wings including a concave surface corresponding to the convex surfaces of the hoops;
        a hole in a first one of said wings, said hole including an opening in the planar surface of said first one of said wings, and said opening having smaller dimensions than said hole;
        a stop ball slidably mounted in said hole and having dimensions greater than said opening;
        a transverse bore in said first one of said wings and extending substantially parallel to the planar surface of said first one of said wings and substantially perpendicular to said hole, said transverse bore being in open communication with said hole and being internally threaded; and
        a screw screw-threadedly received in said transverse bore, said screw having an end which protrudes in said hole into contact with said stop ball to press said stop ball particularly out of said opening to prevent escape of the hoop from the block.

2. A device according to claim 1 further comprising:
    a support including:
        a passage,
        a transverse housing,
        a nut contained in said housing, and one of a mortise and tenon externally thereof;
    an externally threaded sheath provided in said passage and cooperating with said nut, said sheath including an inner narrow axial channel for receiving a pin and an external axial groove;
    a cleat in said support, said cleat slidably positioned in said external axial groove;
    wherein one wing of each block externally includes the other of the mortise and tenon for engagement with one of the mortise and tenon of the support; and wherein rotation of the nut causes displacement of the sheath in the support so as to place the pin under tension or compression with respect to the bone element.

3. A device according to claim 2, wherein said sheath further includes a radial bore in communication with said inner axial channel and screw means screw-threadedly received in said radial bore for engaging and locking the pin in the inner axial channel.

4. A device according to claim 1, wherein each pin support includes a wedge connected to one of the wings of a respective block, said wing including a bore and said wedge including an axle movable within said bore to provide an adjustable connection between the wedge and the respective wing, said bore extending substantially perpendicular to said flattened surfaces of the hoop.

5. A device according to claim 4, wherein the respective block includes a threaded hole in communication with said bore; and further including a radial blocking screw screw-threadedly received in the threaded hole for locking the wedge with the respective block.

6. A device according to claim 5, wherein the axle of the wedge includes an intermediary groove into which the radial blocking screw penetrates for locking the axle in the bore.

7. A device according to claim 1, wherein each hoop is comprised of two half hoops and two rectilinear extension means for connecting the two half hoops together and providing a cross-section substantially identical to a cross-section of the hoop, each extension means including an extension piece comprising connecting members at opposite ends thereof.

8. A device according to claim 7, wherein each connecting member includes a protruding tip on one of a half hoop or an extension means and penetrating respectively within a seat of the same outline provided in the other of the extension means and half hoop; and further including at least one transverse screw for locking the extension means and the half hoop together.

9. A device according to claim 8, further including at least one assembly of double collars associated with a respective hoop, each assembly constituted by two pairs of jaws, and a common transverse axle for connecting the two pair of jaws together, one pair of jaws being adapted to tighten the hoop and the other pair of jaws connected to an end of one of said adjustable braces.

10. A device according to claim 9, wherein each adjustable brace is constituted by two parts movable toward and away from each other along a comon axis, and an intermediary turnbuckle including a rod having opposite ends threaded in opposite directions with respective nuts integral with opposing ends of said two parts of each adjustable brace.

11. A device according to claim 10, further including a bar having successive passages for the fixation of a pin support, telescopically disposed with respect to the hoop, and connected with one of the two pair of jaws of a double collar.

* * * * *